United States Patent
Hunt et al.

(10) Patent No.: US 10,670,438 B2
(45) Date of Patent: Jun. 2, 2020

(54) METHOD AND APPARATUS FOR DETERMINING PROPERTIES OF A CONTAINED FLUID

(71) Applicant: Atout Process Limited, Bridport (GB)

(72) Inventors: Andrew Hunt, New Milton (GB); Richard Foster-Turner, Broadmayne (GB)

(73) Assignee: Atout Process Limited, Bridport (GB)

( * ) Notice: Subject to any disclaimer, the term of this patent is extended or adjusted under 35 U.S.C. 154(b) by 0 days.

(21) Appl. No.: 16/560,051

(22) Filed: Sep. 4, 2019

(65) Prior Publication Data
US 2020/0003670 A1   Jan. 2, 2020

Related U.S. Application Data

(62) Division of application No. 15/409,040, filed on Jan. 18, 2017.

(30) Foreign Application Priority Data

Jan. 21, 2016 (GB) .................................. 1601149.6

(51) Int. Cl.
*G01F 1/64* (2006.01)
*G01N 9/00* (2006.01)
*G01N 27/22* (2006.01)
*G01F 1/74* (2006.01)

(52) U.S. Cl.
CPC .................. *G01F 1/64* (2013.01); *G01F 1/74* (2013.01); *G01N 9/00* (2013.01); *G01N 27/22* (2013.01); *G01N 27/221* (2013.01); *G01N 2027/222* (2013.01)

(58) Field of Classification Search
CPC .. G01F 1/64; G01F 1/74; G01N 27/22; G01N 27/221
See application file for complete search history.

(56) References Cited

U.S. PATENT DOCUMENTS

2013/0346035 A1* 12/2013 Madasu .................. E21B 47/10 703/2
2018/0347341 A1* 12/2018 Huang .................... E21B 47/10

* cited by examiner

*Primary Examiner* — Paul M. West
(74) *Attorney, Agent, or Firm* — Nutter McClennen & Fish LLP

(57) ABSTRACT

In order to measure a fluid flow or flow conditions of a fluid flow through an apparatus, electrodes are provided across which capacitance values are determined. The capacitances are used in conjunction with a predetermined model to determine a revised model for the system. If the modelled to be satisfactory, then the values representative of the flow conditions are output. If it is not, then the model is tuned to reduce the error. A novel arrangement of electrodes is also provided along with apparatus embodying the method. The invention also provides a way of determining fluid properties, for example, density, volume present contained within a vessel or tank whether flowing or stationary.

10 Claims, 15 Drawing Sheets

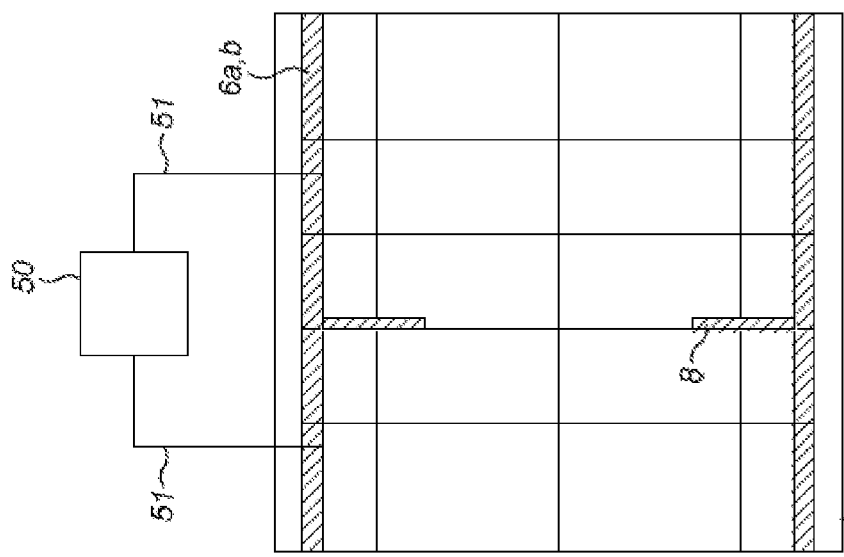
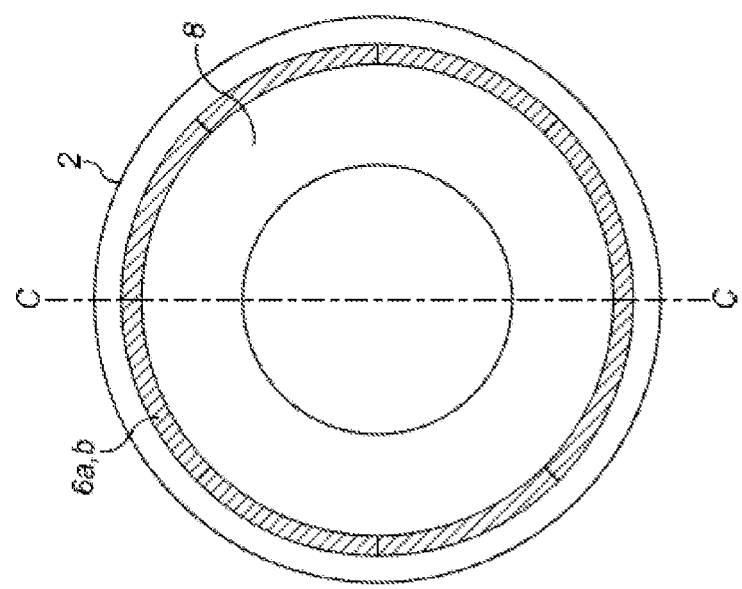
FIG. 5b
FIG. 5a

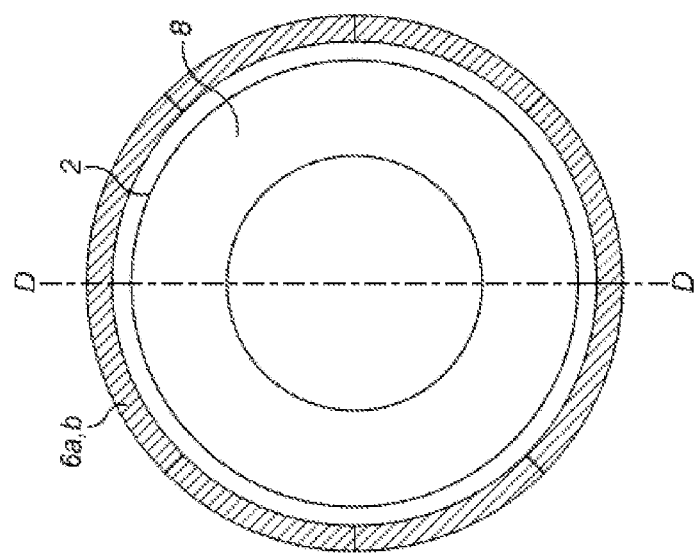
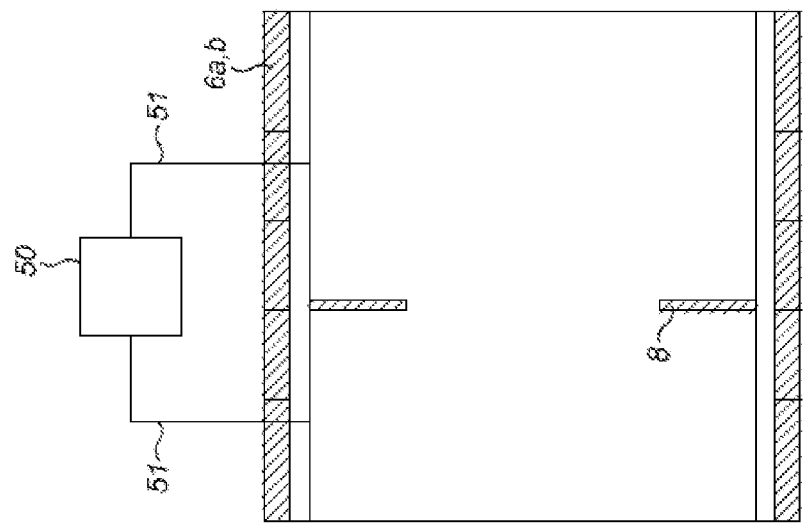
FIG. 6a
FIG. 6b

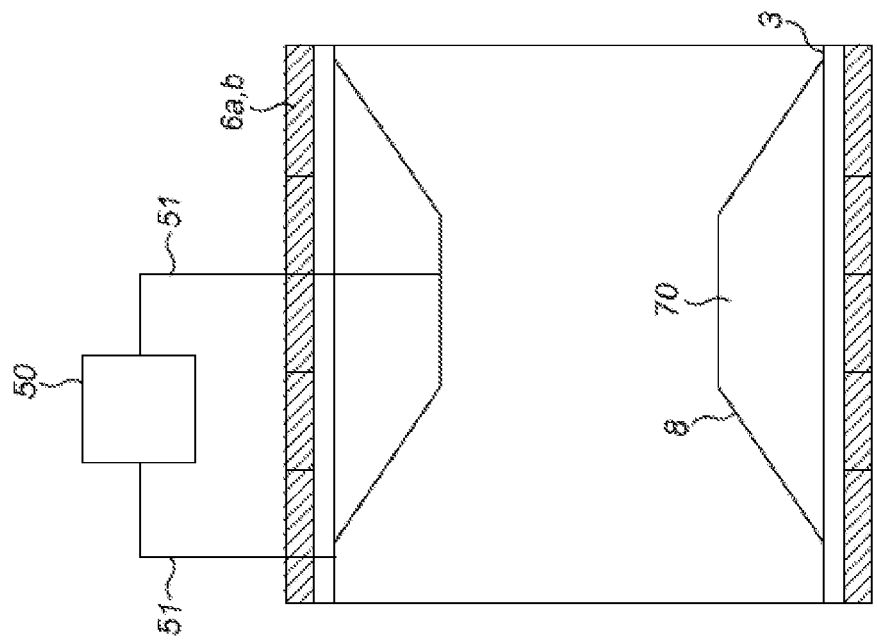
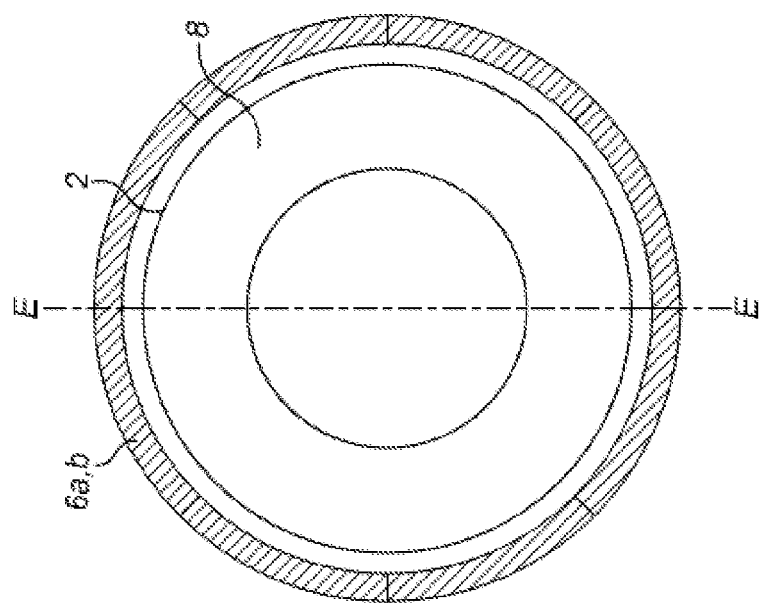
FIG. 7b
FIG. 7a

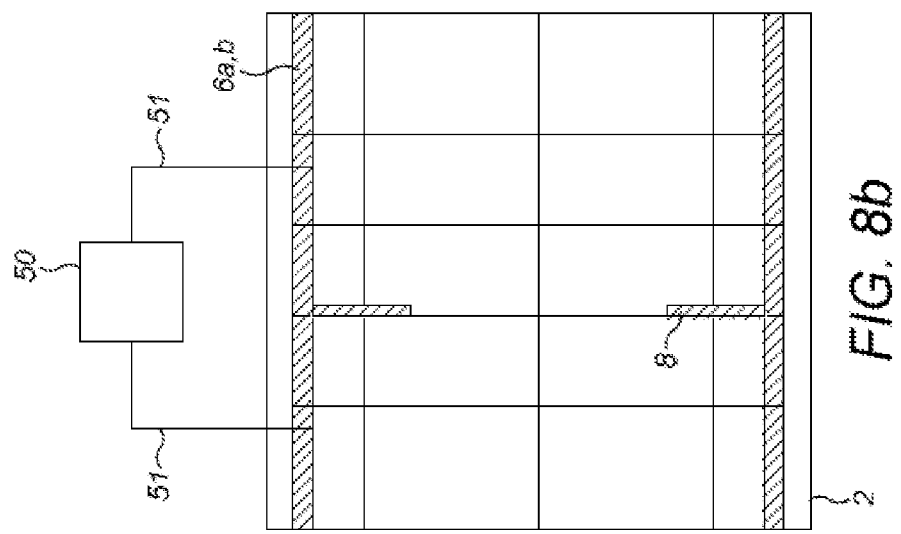
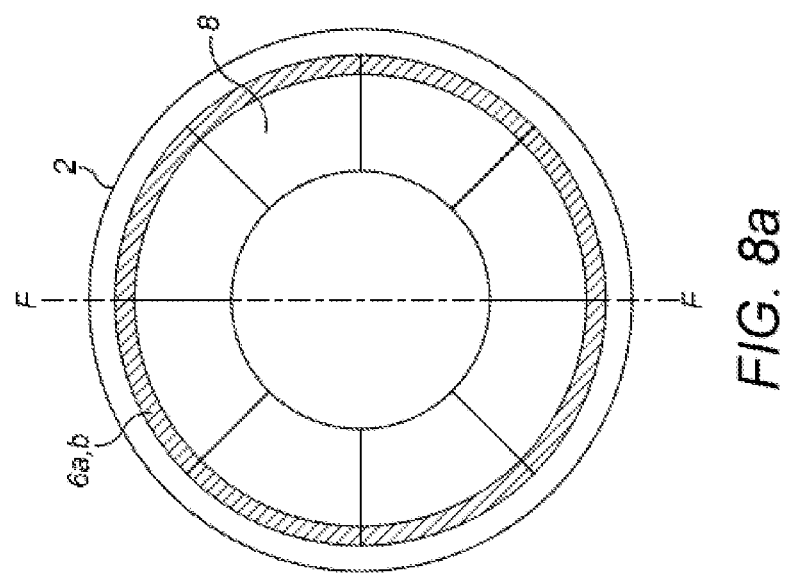

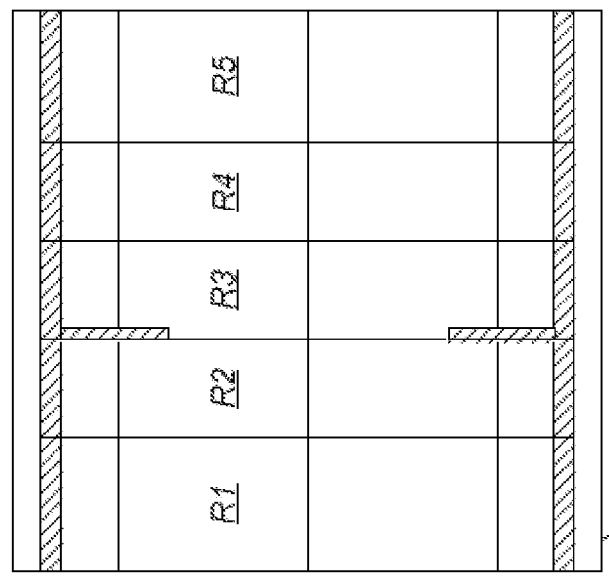
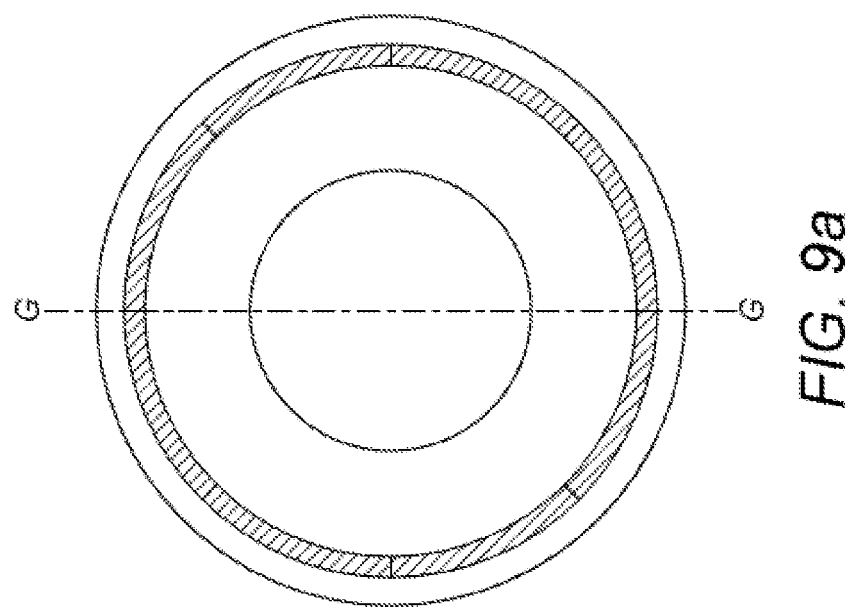
FIG. 9b
FIG. 9a

METHOD AND APPARATUS FOR DETERMINING PROPERTIES OF A CONTAINED FLUID

CROSS REFERENCE

This application is a divisional application of U.S. Ser. No. 15/409,040, which claims priority to United Kingdom application number GB 1601149.6 filed Jan. 21, 2016, the disclosure of each of which is hereby incorporated by reference in its entirety.

FIELD OF THE INVENTION

This invention relates to methods and apparatus for the measurement of mixtures of fluids, or solids and mixtures of both in pipes, tanks and vessels.

BACKGROUND TO THE INVENTION

The storage and flow of mixtures of fluids and solids is widespread in industry. Such flows include pure gas, wet gas, pneumatic conveying of dry solids, slurry flows, sewage, and multiphase flows in the oil industry. Flows occur in many industries including power generation, water and waste treatment, oil and gas production, the food industry, mining, and the chemical industry. Consideration of flow is also important in applications such as aircraft with respect to gas flow through engines and indeed airflow passing an airframe or other components such as engine blades or ducts.

The multiphase mixture of materials to be measured may be flowing along a pipeline, or recirculating within a vessel, including for example fuel or propellant tanks in vehicles, aircraft, spacecraft or satellites.

The liquids may be water, as in wet steam flows, oil or gas condensate, or any other fluid that is liquid at the pressure and temperature of the pipe or pipeline within which it is contained. The phases, gas, solid and liquid, have a number of properties. They may be miscible—as in oil/gas or water/steam combinations, or immiscible as in water/gas or oil/air mixtures. The materials may be electrically conducting, as for example water, or non-conducting. The phases may be in thermodynamic equilibrium with mass interchange between the phases, as in water/steam or condensate/gas, or with no interchange such as when water is flowing in natural gas.

It is known that in pipeline flows or within storage tanks the flow may not have an even distribution. Only a fraction of the pipe or tank may be "occupied". It is known in the art to consider the phases of the gas, liquid or solids entrained and to refer to a first phase and a second phase to differentiate between, for example, the water and the gas within which the water is dispersed. In this example, the water could be termed the first phase and the gas the second phase.

Pneumatic conveying is a further application where a fraction of the flow pipe is occupied by a dispersed second phase, in this case dispersed solids such as grains, minerals and powders are carried by an air or gas which is the first phase. The air or gas is pumped through the system to give the motive power to convey the solids which may flow as a sliding bed, in wave-like structures or dispersed in the flow.

Conveying of solids may also be undertaken by water or other liquids, sewage being a typical example.

Fluid flows which may include entrained liquid, gas or solids are thus widespread in many industries and with many different combinations of gas, solid and liquid. It should be understood that the invention described here applies to any flow or storage of gas or mixture of gas, solid and liquid in any or all of such industries and conditions, the examples above are not regarded as exclusive. The term industrial should not be taken to be limited to a process carried out for the purpose of manufacture or product delivery. It should be interpreted broadly to include the detection of parameters in fluid flows whether they are involved in an industrial process or not.

The fluids in a multiphase flow may be distributed in the direction of flow in many ways. For example, it may be distributed as droplets, bubbles, waves, or wisps within the main body of the flow; as a film on the surface of the pipe or as a continuous medium with the other phases distributed within. In all cases, the liquids or gases will normally be travelling at different velocities, with some phases moving less quickly than others with this being known in the art as "slippage". The difference between a local gas velocity and a local liquid velocity is called the local slip velocity, while the difference between some average of the gas velocity and some average of the liquid velocity is known as the average slip velocity.

Similar conditions exist in conveying of solids in gases or liquids where the solids may be distributed across the flow in many forms at various densities and may be moving at a different velocity to the main flow. The flow is often quantified by reference to a mass flow rate that being the mass of substance which passes a point per unit of time.

The mass flowrate of gas in wet gas flows is normally of significant commercial importance, as, for example, in the transfer of natural gas or steam for sale, or in the management of the process, such as in power generation where the steam mass flowrate is the primary energy input to a turbine. The term wet gas is used here in a general sense to describe any flow that contains significant quantities of gas carrying with it some quantity of a liquid or mixture of liquids. The mass flowrate of liquid may also have a financial cash value, as in gas condensate flowing from a gas production unit, it may be important for technical management as in supply to a steam turbine, or it may have no particular financial value/importance, as in supply of steam for heating. The measurement of the flow may be required for taxation purposes referred to in the art as a "fiscal measurement".

In many applications, it is not the mass flowrate of gas or liquid in the conveying system but the flowrate of the dispersed solid that is of critical interest to the operator of the process.

In order to meter the flow of such fluid and solid mixtures, standard single-phase flowmeters such as orifice plates, venturi meters or vibrating tube mass flowmeters are presently used and the liquid flowing in the wet gas, or the solid present in the gas or liquid, is effectively a contaminant which modifies the behavior or calibration of the device from its normal behavior in single-phase flows. A correction is carried out.

The correction of the reading of a gas meter used in wet gas or pneumatic conveying depends on the quantity of liquid or solid flowing, and also on the distribution of the liquid or solid in the pipe and the slip velocity. Similarly, the correction of the reading of a liquid meter used in solids conveying depends on the quantity of liquid flowing, and also on the distribution of the liquid in the pipe and the slip velocity Since normally the distribution and velocity of the distributed liquid or solid is not measured, assumptions are made which increase the uncertainty of the indicated value of flowrate. Because of the wide range of multiphase industrial flows and their substantial commercial importance, the resultant potential financial uncertainty is very significant.

Many of the state-of-the art methods for measuring flowrate include a differential pressure measurement. Examples include orifice plates and venturis. These methods and the meters that embody them are widespread and relatively low cost but suffer from significant limitations including:

- differential pressure devices may be used which are, by their nature, delicate relative to the level of pressure in the pipe and can be destroyed by pressure pulses in the flow;
- using robust absolute pressure measurement sensors limits the resolution of the measurement because they use a method which involves taking the difference of two values each of which is large relative to the absolute value of the difference; and
- small discontinuities in the tubes (to provide pressure ports) linking the flow to the sensors which may add substantial error which is not appreciated and compensated for by the user.

Other multiphase flows in addition to the wet gas flows described above contain a mixture of materials, variously gas, liquid, divided solids and combinations thereof, and there are a variety of flow regimes or patterns that occur. For example, a gas may flow smoothly over the top of a liquid layer in a horizontal pipe, large bubbles may fill the pipe intermittently, slurries or solids may move in waves, or the flow may even plug and stop completely. Many other flow patterns may occur in diverse mixtures. Each of these flow regimes or patterns may have commercially or technically important implications, for example the energy used to transport the fluids may vary with flow regime, the mixing between the phases may be important in the process and will vary with flow regime, it may be important that certain of the phases do not touch the internal surface of the pipe, some flow regimes may lead to more erosion or deposition than others, and different flow regimes may influence the output from conventional flow sensors in such a way that measurements made of the flow are not correct.

It is envisaged that the invention will be applicable to many or all of the above flow types and others. The described specific embodiments are illustrative to provide an understanding of the invention and should not be taken to limit the invention the depicted applications or particular arrangements.

A number of physical principles have been used to visualize internal flow processes in industrial pipes or vessels, these are referred to, in general, as flow imaging or process imaging. Such methods include the measurement of electrical capacitance, electrical conductivity, x-rays, gamma-rays, nuclear magnetic resonance, magnetic fields or nucleonic emission of particles and a determination of how they vary across the length and breadth of the flow.

Many of the "imaging" techniques have been applied in research tests and pilot-scale plants but few are in wide-scale use in industrial applications. For example: CN2826373 (Y) discloses image pick-up tracking and detecting system, GB2212903 (A) describes x-ray stereoscopic imaging system, CN1344929 (A) discloses resistance chromatographic instrument, CN102410974 (A) discloses pulse laser sources, WO2012031292 (A1) discloses ultrasonic scanning, WO2012100385 (A1) discloses a gamma ray imaging device, KR100815210 (B1) discloses a 3D particle mage velocity meter, JP2004212117 (A) discloses X-ray. US2011109308 (A1) and US2012174684 (A1) describe magnetic resonance and CN102364046 (A) discloses light intensity modulation type optical fiber sensors.

Normally such imaging techniques are used to show a cross-section of the pipe normal to the flow direction or a longitudinal section along the flow direction but more recent developments have led to 3-dimensional imaging of the body of the flows. For example: JP2004333237 (A) describes a method to reconfigure the visualization image of a mixed flow in a fluid transport pipe by process tomography and CN2695964 (Y) describes discloses an oil-gas two-phase flow investigating device based-on capacitive chromatographic imaging system.

Flow imaging techniques such as ECT (Electrical Capacitance Tomography) have been developed into working flowmeters for certain applications and other of the techniques are used as part of the technology of multiphase flow metering. GB2390683 (B) describes a flow meter based on electrical capacitance tomography wherein image data sets representing concentration are used to calculate flowrates of multiphase flows and for example Hunt, Pendleton and Byars in 2004 described in (2004) "Non-intrusive measurement of volume and mass using electrical capacitance tomography" ESDA 2004-58398, 7th biennial ASME conference, Jul. 19-22 2004, Manchester UK, a method of estimating volume and mass of solid objects using ECT, while Hunt Pendleton and Ladam in 2004 in "Visualisation of two-phase gas-liquid pipe flow using electrical capacitance tomography" ESDA 2004-58396, 7th biennial ASME conference, Jul. 19-22 2004, Manchester UK, described measurements of flow structures in mixtures of oil and gas. In all three of these references, as in other publications, the ECT sensors are calibrated so as to measure the fraction of volume that each phase is present in any given volume of the pipe. This fraction is known as the "volume fraction" or "holdup".

The difficulties of implementing flow or process imaging in industrial applications include the cost—such devices often cost ten times or more the cost of standard flow meters or other sensors; the danger and complexity of implementing nucleonic measurements in standard industrial processes; and the practical difficulty of making complex measurements of this kind in pipes at high pressure and temperature. In addition, knowledge of the volume fraction may not be sufficient or appropriate. The inventor of the present application made the realization that knowledge of the density distribution in the pipe may be more helpful.

A particular problem arises in propellant/fuel or other fluid storage vessels in space vehicles and that is determining how much of the propellant/fuel remains within the vessel and or associated pipework. As the fluid is used under low or zero gravity conditions, it disperses as droplets in a mixture of sizes with empty space between. This makes it difficult using traditional methods to determine the volume remaining and assumptions based on "burn time" consumption after first filling are used to provide an estimate. As will be appreciated, this can lead to tanks being filled with more propellant/fuel than is actually needed to provide a "safety margin". Given the very high costs per kilogram of launching vehicles or satellites into space, the cost of launching into space are greatly added to by the excess fluid/propellant/fuel.

SUMMARY OF THE INVENTION

An aspect of the invention provides method for determining the density of the various phases in a multiphase fluid within a pipe or tank by: providing an arrangement of electrodes to, in use, be exposed to a fluid mixture either directly or through an insulating layer; providing the fluid mixture; repeatedly measuring a set of capacitances from the set of electrodes; generating tomographic pixelated images of the permittivity distribution within the mixture from each set of measured capacitances at each point in time; generating a set of probability density functions for the value of each pixel location within the pixelated images against time; maintaining a continuous record of the probability density function against time; deriving the density or other physical or chemical property of the two fluids from the probability density functions.

Another aspect of the invention provides methods for determining a flow of a fluid comprising the steps of: providing an arrangement of electrodes to, in use, be exposed to a fluid flow; providing a first model of a fluid flow for a particular arrangement of electrodes; providing a set of penalty functions; providing the fluid flow; determining from the electrodes a set of capacitance values; deriving from the set of values and the first model a second model of fluid flow; comparing the second model of fluid flow with the set of values to provide a global system penalty; and comparing the global system penalty with a predetermined threshold value and, responsive to the comparison, modifying the first model or outputting a rate of flow determined from the set of values and the second model of fluid flow.

A broad aspect of the invention described herein is a method for measuring density of individual phases within a pipe or vessel from a tomographic image of measured electrical properties. The measured electrical property at a point in space and time is a function of fluid density, which in the case of capacitance normally a simple linear function, and the probability density function of the measured electrical property will indicate the range of densities present over time. If the representative measurement volume is small, then the maximum and minimum values of the probability density function measured over any time period will represent the maximum and minimum values of density in the flow at that point. The density of a gas is a strong function of pressure, while the density of a liquid is not. This invention allows the measurement of fluid flow through the method presented below, and also enables long-term self-calibration of measurements of mass of liquid in a vessel (for example, where a storage tank is not readily accessible such as in an unmanned spacecraft). Since the density of a liquid is not a strong function of pressure, the upper point on the probability density function can be used for calibration of the sensor system while the lower point can be used to infer the pressure within the vessel.

The invention provides in a further aspect, a method and apparatus for determining the amount of a liquid within a storage vessel or pipe.

In another aspect of the invention there is provided a method of determining a rate of flow if a fluid or mixture of fluids and or solids and a corresponding apparatus.

According to the invention there is provided a method of determining the rate of flow of a fluid or mixture of fluids or solids and fluids by the steps of: channeling the flow within a channel to define a direction of flow; generating a pressure drop in a region of the channel; providing a set of sensors for sensing electrical parameters at, at least, a first and a second position, which at least first position being at a first side of the pressure drop, and the at least second position on the other side of the pressure drop with respect to the direction of fluid flow which electrical parameters being dependent on the composition and physical properties of the flow and fluids in the flow; measuring the pressure drop; determining from the sensed electrical parameters values the physical properties of the fluids before and after the region where the pressure drop occurs and determining from the values a correction factor; and determining the mass flowrate of one or more phases in the fluid flow from the correction factor and the measured pressure drop.

The invention provides in a further aspect apparatus for determining the pressure drop which apparatus comprising: means to channel a fluid flow; means for generating a pressure drop in the fluid flow; a plurality of sensors for sensing electrical parameters at at least a first and a second position, which at least first position being at a first side of the pressure drop and the at least second position on the other side of the pressure drop with respect to the direction of fluid flow which electrical parameters being dependent on the composition and physical properties of the flow and fluids flowing; means for determining from the sensed electrical parameters values for the fluid flow properties; means to determine the pressure drop from the measured fluid properties.

Preferably, having determined the pressure drop the apparatus may include further means to derive the flowrate of fluids from the measurement of pressure drop in the conventional manner through use of a relationship or mathematical equation relating pressure drop and flowrate, such as, for example the Bernoulli equation.

The invention provides in a yet further aspect, apparatus for determining the rate of flow of a fluid or mixture of fluids or solids and fluids which apparatus comprising: means to channel a fluid flow; means for generating a pressure drop in the fluid flow; a plurality of sensors for sensing electrical parameters at at least a first and a second position, which at least first position being at a first side of the pressure drop and the at least second position on the other side of the pressure drop with respect to the direction of fluid flow which electrical parameters being dependent on the composition and physical properties of the flow and fluids flowing; means for determining from the sensed electrical parameters values for the fluid flow properties; means to determine the mass flowrate of one or more of the materials flowing from the fluid properties so measured.

The preferred method and apparatus use a tomography method for determining the fluid properties and flow mass.

The various aspects of the invention provide substantial advantages over the prior art in that they provide robust apparatus with few or no moving parts, provide an independent measurement of the mass flowrate of liquid in the wet gas flow. In addition, the invention may provide measurement of the liquid, gas and solids distribution and velocity which may be used independently or in conjunction with a standard gas flowmeter to improve the accuracy of that device.

In broad terms, the method in an aspect of the invention comprises the following steps:

(1) Create a small pressure drop along the flow direction by mounting an orifice plate, venturi throat, nozzle or other obstructive or restrictive device within the flow.

(2) Measure the distribution in both time and space of an electromagnetic parameter, such as capacitance or resistance, before, or in the vicinity before, the obstructive device, and after the obstructive device. Determining a probability density function before and after the obstructive device representing conditions at various positions within the flow. The measured electrical property at a point in space and time is a function of fluid density—in the case of capacitance normally a simple linear function—and the probability density function will show the range of densities present over time. If the representative measurement volume is small then the maximum and minimum values of the probability density function measured over any time period will represent the maximum and minimum values of density in the flow at that point. In the case of a wet gas carrying a non-conducting liquid such as a hydrocarbon, the change in gas density derived from the lower point of the probability density function may be used to derive the pressure at that point, while the liquid density derived from the upper point of the probability density function may be used to derive the density of the liquid.

(3) Use the probability density functions determined to derive the liquid and gas densities or other physical or chemical properties before and after the obstructive device.

There are then three options, either:

(4) Use the thus measured fluid density before and after the obstructive device to derive a correction factor to correct a measurement of flowrate derived from a separately measured pressure drop across the constriction;

or:

(5) Use the measured fluid density before and after the obstructive device to infer the pressure drop, thus removing the need for a separate means of measuring pressure drop;

or:

(6) Use the measured electrical parameters directly through a model or artificial intelligence system to directly infer the flowrate of fluids.

A further aspect of the invention provides a method for determining the density of two phases in a multiphase flow by: providing an arrangement of electrodes to, in use, be exposed to a fluid flow, providing the fluid flow, measuring a set of capacitances or resistance values from the set of electrodes, generating a set of probability density functions for the measured capacitances, deriving the density or other physical or chemical property of the two fluids from the probability density function.

In further preferred methods and apparatus, multiple electrode arrays may be mounted upstream of the obstructive or constrictive device, at the throat of the obstructive device, at the vena contracta of the obstructive device or downstream of the obstructive device. Multiple comparisons may be made to infer the flowrate and concentration of material.

Aspects of the invention may be used to provide a method and apparatus for monitoring flow over a surface such as an engine blade or aerofoil.

BRIEF DESCRIPTION OF THE DRAWINGS

Specific embodiments of the invention will now be described, by way of example only, with reference to, the figures in which:

FIGS. 5A, 5B, 6A, 6B, 7A, 7B, 8A, 8B, 9A, 9B, 10A, 10B, 11, 12A, and 12B are further embodiments of the invention;

DETAILED DESCRIPTION OF EMBODIMENTS OF THE INVENTION

Figure 1:
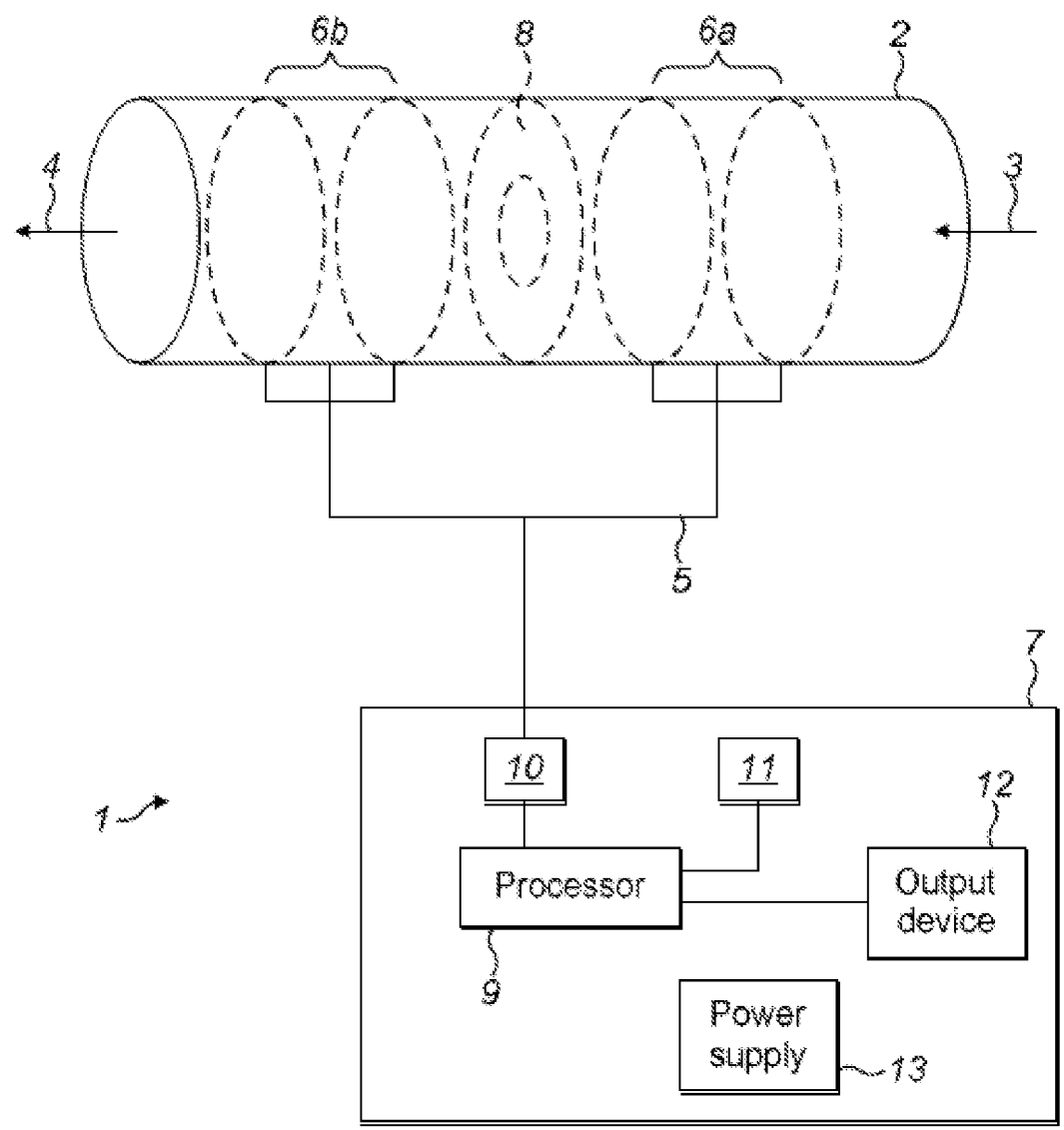
FIG. 1 is an overview of an apparatus for measuring fluid flow in accordance with the invention.

As is shown in FIG. 1, a flow sensing device apparatus 1 in accordance with the invention comprises a set of electrodes 6 generally indicated at a location in or about a pipe 2 within which a flow is contained. The pipe is shown as a limited length longitudinal section but will be understood to extend over a great length from a source of supply (not shown) to an outlet (not shown). The flow has a direction as indicated by labelled arrows 3 and 4. A wire bus 5 is provided to link the electrodes 6 to a fluid flow analyser 7.

Within the pipe 2, and shown in broken outline, is a constriction or obstruction 8. In this case it is depicted as a planar disc with a centrally located hole. The disc acts to constrict the fluid flow to the hole. Other means of causing a pressure drop will be apparent to a person skilled in the art.

The electrodes 6 are arranged to provide electrodes 6a "upstream" of the constriction (to the right in the figure) and "downstream" 6b of the constriction (to the left of the figure). In some embodiments of the invention, the electrodes 6 will be arranged outside of the pipe 2 or internally or within the body of the wall of the pipe. As will be later described, the electrodes provide a set of electrical values in this case capacitance values from which the flow before and after the restriction may be determined to in turn provide a value of the fluid flow through the constriction.

Various forms of the electrodes and the constriction or means to create a pressure drop will be later described.

The flow analyser 7 is a microprocessor based arrangement and comprises a processor 9, an input port 10, a memory 11, an output device 12 such as a visual display unit and a power supply 13. The memory 11 provides storage memory for variables and also a set of instructions (code) for controlling the way in which the microprocessor operates to perform the flow analysis. It includes ROM (read only memory) and RAM (random access memory).

Figure 2:
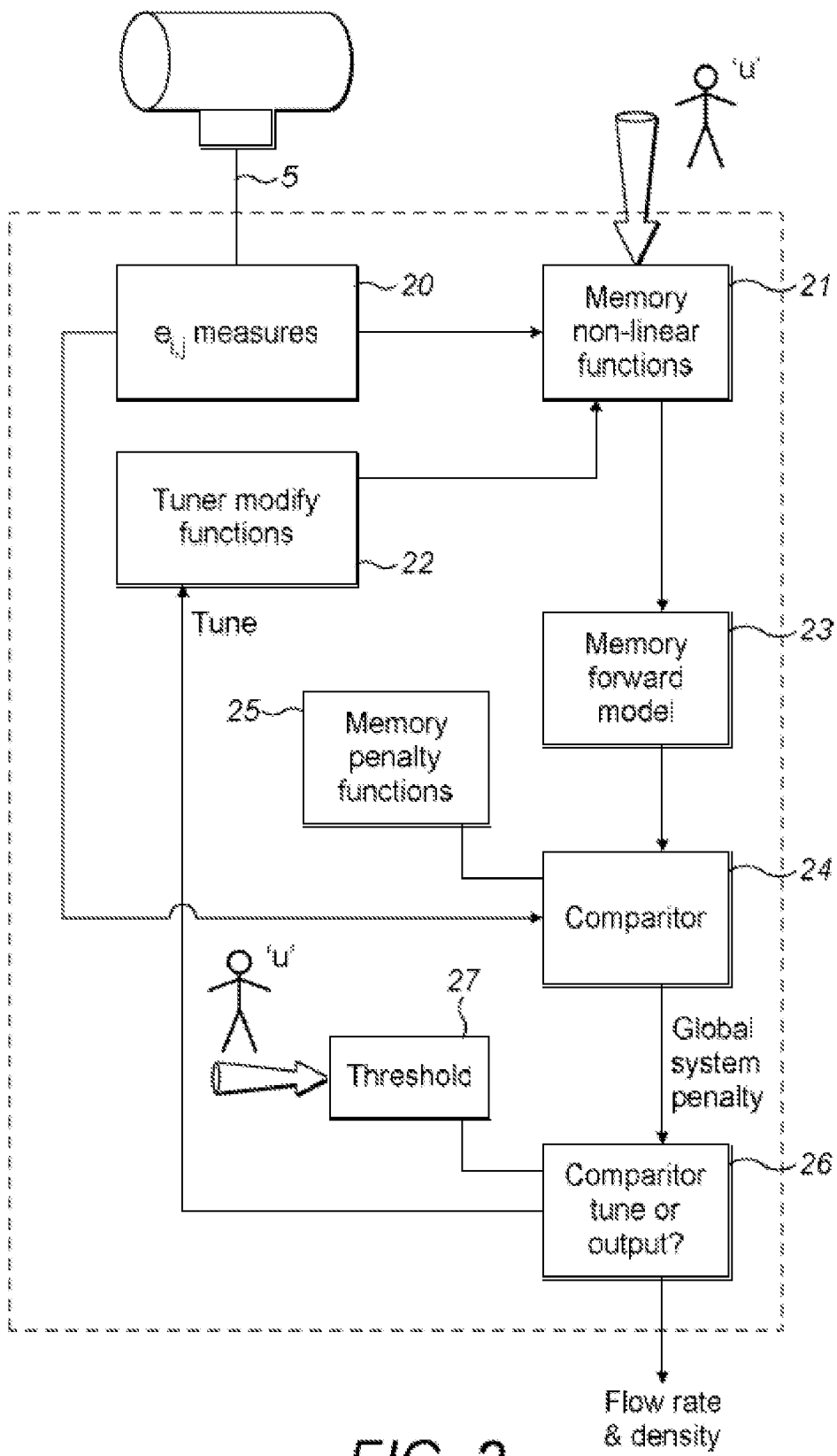
FIG. 2 is a schematic diagram showing blocks of functionality provide by a processor forming part of the apparatus shown in FIG. 1.

The processor 9 is governed by the set of executable instructions to provide blocks of functionality which are shown schematically in FIG. 2. It will be appreciated that these blocks of functionality may be all or in part replicated by circuitry produced as discrete electronic components or a mixture of such components and processors programmed to provide elements of the functionality.

FIG. 2 shows a set of functions provided by the programmed processor 9 and the way in which they interoperate. The processor 9 provides a first block of functionality 20 which determines a set of e(ij) measures for the electrode combinations which are values of capacitance at particular points in time. These measurements may be made, for example, by means well known to a person skilled in the art and which are commercially available, for example, from Atout Process Ltd (www.atoutprocess.com).

These values of e(ij) are output to a memory 21 which holds a set of pre-programmed non-linear functions. These are defined and loaded into the memory by a user "U" in a pre-use calibration step. The non-linear functions represent the way in which the capacitance varies between the electrodes at different flow rates and conditions. They are a set of representative parameters for an average pipe. The actual performance represented by the measured values of e(ij) will vary from this set of equations. It is a model of a typical system and may be termed a reverse model in the sense that it provides a set of capacitances which would be detected for the modelled system, at particular flow rates and conditions, whereas the intention for the apparatus is to provide from a set of measured capacitances a determined flow.

In this particular embodiment, the pre-loaded non-linear functions are the following:

$$rho(ij)=Q(M(ij))$$

$$Ku(ij)=G(rho(ij))$$

$$e(ij)=F(Ku(ij))$$

where in a calibration at manufacture of the device a set of fixed relative permittivities Ku may be provided, for example by filling the pipe with a gas or liquid and performing measurements of e(ij) at a range of pressures so that the function rho(ij) is known and the form of F and G may be directly calculated from calibration data of known reference rho(ij) related to measured e(ij).

F and G are a set of functions derived for each sensor at the time of calibration during manufacture. The forms of F and G will be generally developed for each electrode pair and the coefficients fitted ideally through a multi-point calibration—empty, and then full of a well-defined reference product.

e(ij) is expressed in units of Farads, typically ranging from 10 to 1000 fF. Ku is expressed in units of non-dimensional relative permittivity where air (sensor empty) has a value of 1 and mineral oil (for example) is in the order of 2.5. F and G may also be derived from modelling of the sensor using mathematical or numerical models.

Q is a set of functions derived at the time of installation or laboratory calibration by flowing a known fluid at a range of known flowrates. The form of Q will be generally developed for each electrode pair and the coefficients fitted ideally through a multi-point calibration. Q may also be derived from modelling of the sensor using mathematical or numerical models.

M(ij) is thus the output measured mass flowrate over the area represented by the measurement of electrode pair capacitance e(ij) by means of the calibrated or modelled functions F, G and Q. The total mass flowrate of fluid is derived from the sum of all M(ij) and is measured in kg/s or similar units.

The functions F, G and Q are inverted mathematically to their inverse functions F', G' and Q' and stored in memory 21. Inversion is a well-known process, so that for example if F=a then F'=1/a, other more complex functions have more complex inversions well known to practitioners in the art. The set of functions F, G and Q are referred to as the forward model, while F', G' and Q' are referred to as the inverse model.

$$Ku(ij)=F'(e(ij))$$

$$rho(ij)=G'(Ku(ij))$$

$$M(ij)=Q'(rho(ij))$$

The apparatus performs an iterative training to revise the model. In doing this, a tuner function performs a modification of the non-linear functions held in memory 21 by, in this case, changing parameters within the functions. The tuner formed as a network using neural network techniques of nodes and weighted links.

The reverse model held in memory 21 is used to generate output values of flowrate estimate from the measured values of e(ij). In this process, the model is reversed to provide values of flow based on detected capacitances across the various permutations of electrode couplings. This is held as a matrix of values eij loaded into memory 23 and represents a forward model of the apparatus. That is to say, a model which provides a flow from input capacitance values eij.

The forward model stored in memory 23 is then used to calculate what the capacitance values would be if these values were true. These new estimates of capacitance values are referred to as e'(ij)

The resultant forward model is used by a comparator 24 in conjunction with a set of penalty functions held in memory 25 to produce a global system penalty. In this particular example, the penalty functions are:

$$P(ij)=b(ij)\sim(e(ij)\sim e'(ij))$$

and the global penalty is the sum of all individual P(ij) values P*.

The penalty functions P(ij) represent the weighted difference between the measured values and the estimates based on the inverse/forward modelling process and the global penalty P* represents the overall accuracy of the model relative to the true conditions in the pipe. The global system penalty is a measure of how close to the actual system the forward model held in memory 23 is.

The global system penalty is input to a second comparator 26 which compares the value with a threshold held in memory 27. The threshold is provided at an initial calibration step performed by the user "U" at the same time as the initial non-linear functions are loaded into memory 21.

In the event that, the comparator determines that the global system penalty is greater than the threshold in memory 27, then an instruction to "tune" is output to the tuner 22 to modify the functions held in memory 21.

In the event that, the comparator determines that the global system penalty is less than the threshold, then the present flow rate and density values are output.

The modified set of forward and reverse model equations is stored in memory 21 and 23 respectively and may be output as a reference system of equations to start the iterative procedure for other flow conditions which may occur during the lifetime of the measurement installation or in other flow systems of interest to the user.

Various alternative embodiments of the invention will now be described with particular reference to the electrode/sensor elements which may be substituted for those in the above described embodiment. Like elements are identified by the same reference numerals.

Figure 3B:
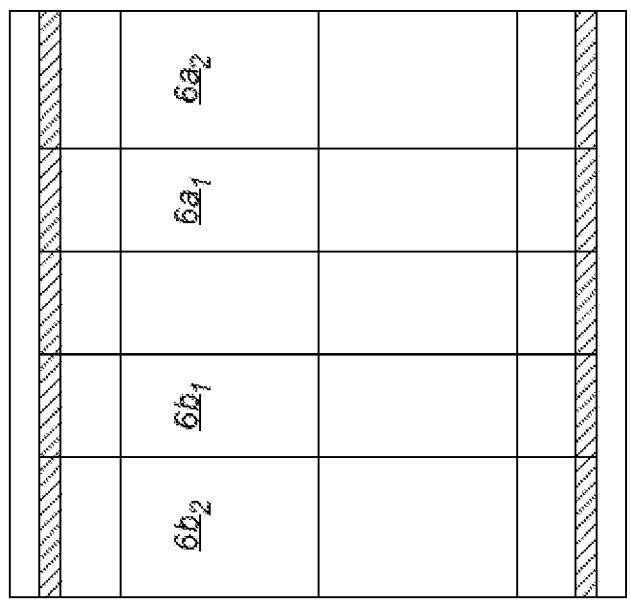
FIG. 3B is a longitudinal section of the pipe shown in FIG. 1 with an internally located set of electrodes circumferentially arranged about the inner periphery of a wall defining the internal bore of the pipe.
Figure 3A:
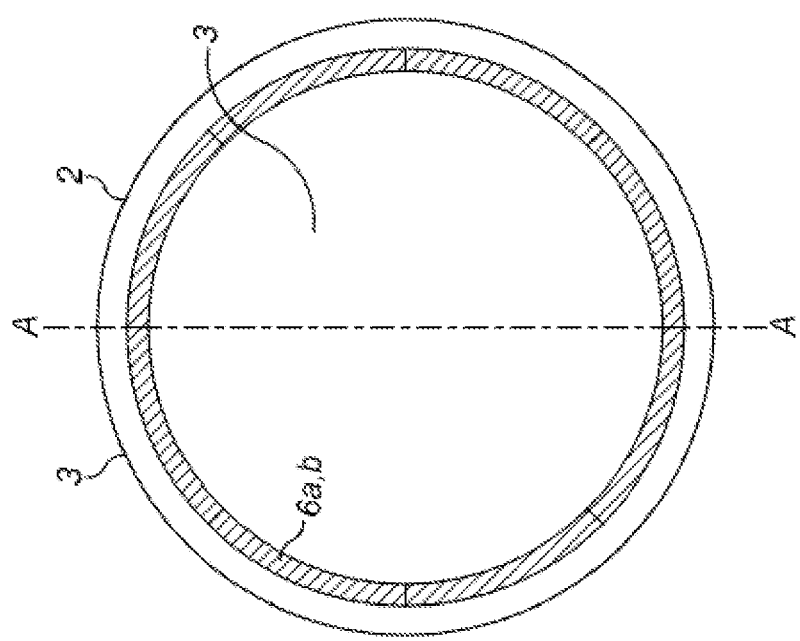
FIG. 3A is a cross-section through within pipe containing fluid flow of interest in accordance with a first embodiment of the invention.

FIG. 3A shows electrodes, coils or other electrical sensing elements as curved rectangles distributed around the inside of a pipe cross-section containing a flow. In this case, the pipe wall is electrically conducting but in other embodiments it may be non-conducting. The electrodes, coils or other electrical sensing elements may be any number or arrangement around the pipe being electrically insulated from each other and from the pipe wall.

As will be apparent from FIG. 3A, the electrodes 6a, 6b number eight encompassing the complete internal diameter of the pipe. As shown in FIG. 3B each electrode extends in the axial direction of the pipe. It will be seen that the electrode 6a1 has the same length in the axial direction as electrode 6b2. Electrode 6a2 is longer that electrode 6a1 but the same length as electrode 6b2. However, whilst this arrangement is preferred alternative dimensions may be used in other embodiments.

Figure 4B:
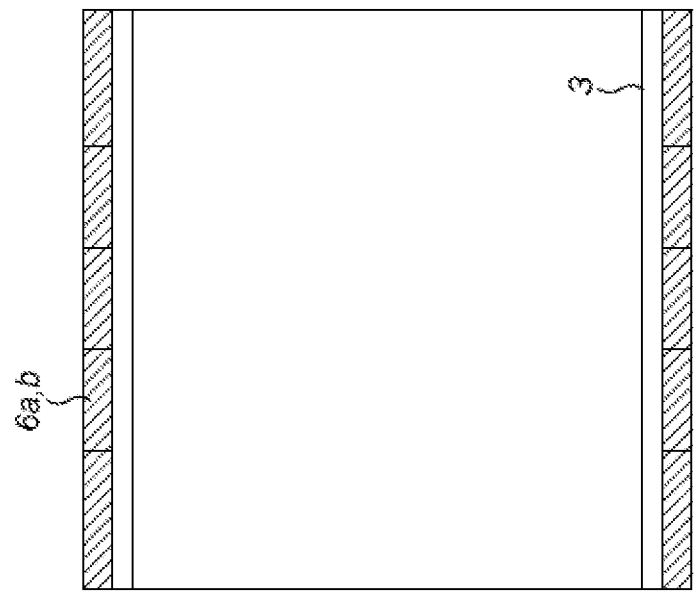
FIG. 4A is a cross-section of a second embodiment of the invention in which electrodes are arranged about the periphery of a pipe containing a fluid flow of interest with FIG. 4B being a longitudinal section.
Figure 4A:
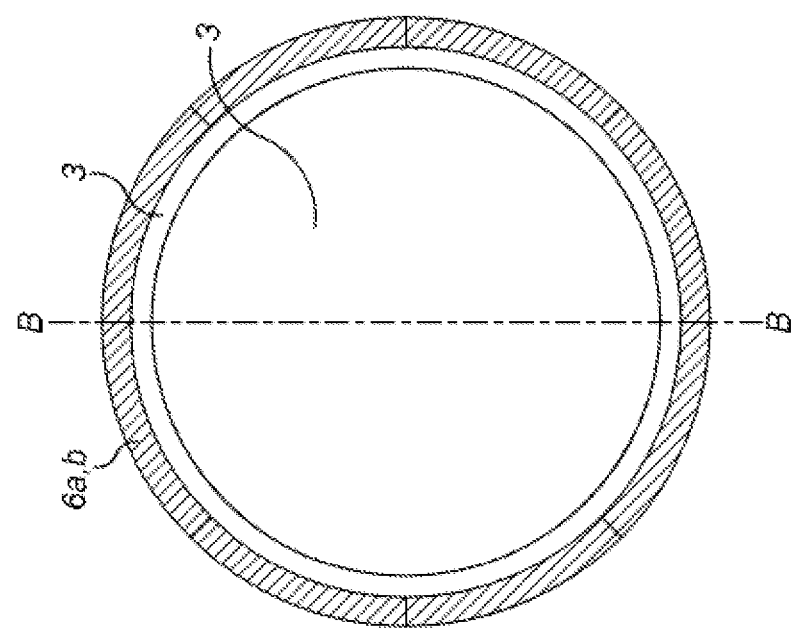

FIG. 4A and 4B show electrodes, coils or other electrical sensing elements as curved rectangles distributed around the outside of a pipe cross-section containing a flow. In this case the pipe wall must be electrically non-conducting or pro a sheath of non-conducting material disposed between the pipe and the electrodes. The electrodes, coils or other electrical sensing elements may be any number, or arrangement around the pipe and are electrically insulated from each other and from the pipe wall.

FIGS. 5A and 5B show a preferred embodiment of the present invention with electrodes, coils or other electrical sensing elements distributed around the inside of a pipe cross-section containing flow at several axial locations relative to a pressure drop device which is in the form of an annular ring or orifice plate. The electrodes, coils or other electrical sensing elements may be any number, shape or arrangement around the pipe and the pressure drop device may be any shape which blocks the flow to some extent. The pressure drop is also measured by the pressure transducer 50 through pressure tappings 51 communicating with the inner surface of the bore of the pipe at positions either side of the constriction 8. This represents a legacy pressure sensing arrangement augmented by the present invention or it may be provided for the purpose of factory calibration.

FIGS. 6A and 6B show a preferred embodiment of the present invention with electrodes, coils or other electrical sensing elements distributed around the inside of a pipe cross-section containing flow at several axial locations relative to a pressure drop device which is in the form of an annular ring or orifice plate. The electrodes, coils or other electrical sensing elements may be any number, shape or arrangement around the pipe and the pressure drop device may be any shape which blocks the flow to some extent. The pressure drop is measured by the pressure transducer 50 through pressure tappings 51.

FIGS. 7A and 7B show a preferred embodiment of the present invention with electrodes, coils or other electrical sensing elements distributed around the outside of a pipe cross-section containing flow at several axial locations relative to a pressure drop device which is in the form of an venturi insert 70. The electrodes, coils or other electrical sensing elements may be any number, shape or arrangement around the pipe and the pressure drop device may be any shape which blocks the flow to some extent. The pressure drop is measured by the pressure transducer 50 through pressure tappings 51.

FIGS. 8A and 8B show a preferred embodiment of the present invention with electrodes, coils or other electrical sensing elements distributed around the inside of a pipe cross-section containing flow at several axial locations relative to a pressure drop device which is in the form of an annular ring or orifice plate. In addition to the electrodes around the pipe there are also electrodes, coils or other sensing elements on either or both surfaces of the pressure drop device. The electrodes, coils or other electrical sensing elements may be any number, shape or arrangement around the pipe and the pressure drop device may be any shape which blocks the flow to some extent. The pressure drop is measured by the pressure transducer 50 through pressure tappings 51. The constriction 8 is this time formed of a segmented plate. The segments of the plate are configured as further electrodes for use in determining the flow.

FIGS. 9A and 9B show a further embodiment in which the electrodes 6 are provided in regions R1 to R5.

Figure 10B:
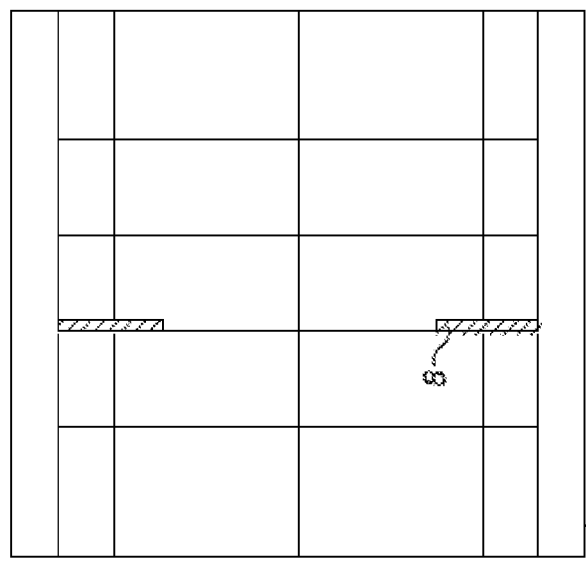
Figure 10A:
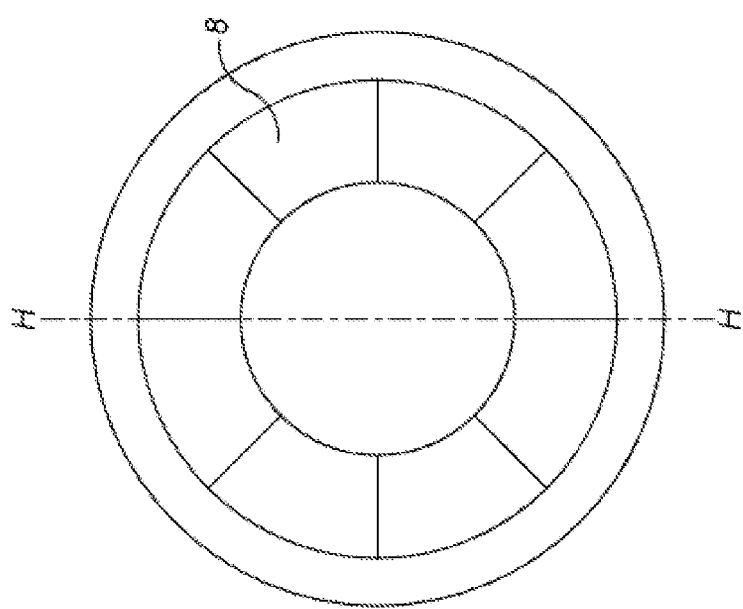

FIGS. 10A and 10B show an embodiment in which the constriction 8 is provided as a plate, the plate itself carries the sensor electrodes hence its apparently segmented appearance when viewed along the direction of flow as shown in FIG. 10A. This preferred, where it is desired to provide a retrofitting of an existing orifice plate. The electrodes may be easily removable from the pipe by means of an orifice-plate carrier, something which is frequently already in place on a pipeline for carrying prior art orifice plates. Commercially then the device can be sold as a direct replacement of a cheap orifice plate, simply fitting in place of the existing replaceable plate, while the pressure drop measurement may be removed entirely, or used as a subsidiary mechanism to improve customer confidence in the capacitance measurement. In this case the electrical connections would be routed through the body of the plate out of the pipe through the carrier access.

Figure 11:
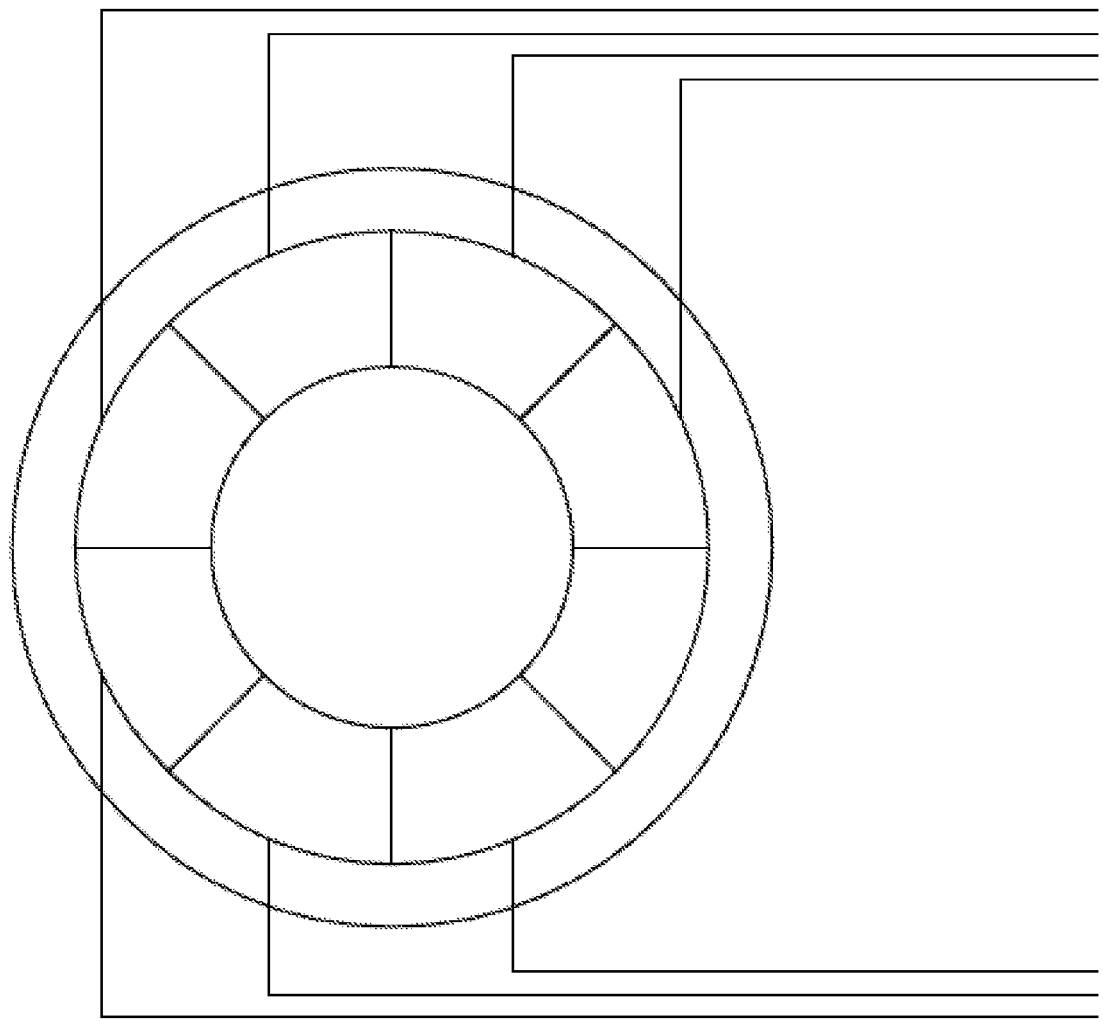

FIG. 11 shows the embodiment of FIGS. 10A and 10B with detail of the way in which the electrodes 6a,b are electrically coupled to the analyser 7.

Figure 12A:
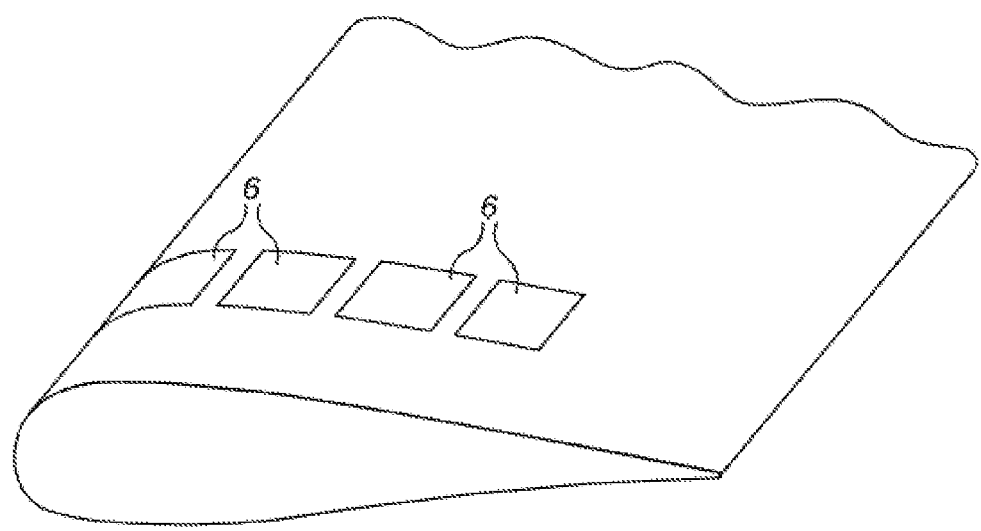
Figure 12B:
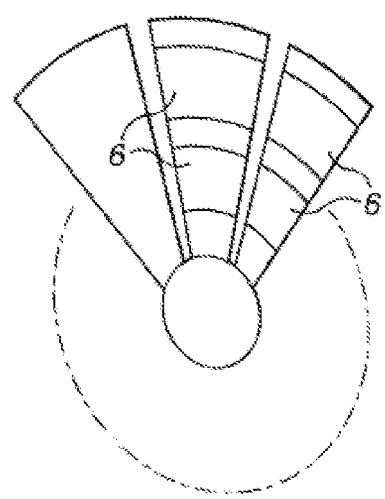

FIG. 12A shows an embodiment in which the electrodes 6 are provided at a surface of the wing of an aircraft. This will be useful for monitoring the flow over the wing surface. Similar arrangements may be provided for determining flow over other vehicles such as boats or submarines. FIG. 12B shows the electrodes provides at the surface of the blades of a fan assembly of a jet engine.

The electrodes may be provided as discrete components or provided as conductive deposited layers. For example, the blade structure of the engine shown in FIG. 12B may be manipulated during manufacture to provide conductive and non-conductive portions as required to provide the electrodes.

The initial step of calibrating the apparatus will now be described.

Calibration

Step 1

The device may be calibrated for one or more particular gases at the time of manufacture or after installation in the case of a retrofit, in the following manner:

1.1 A flow meter is connected to a short length of pipe and pressurised to a range of pressures covering that of interest in the proposed application.

1.2 Measure all capacitances between every pair of electrodes and relate each to the density of gas which is in this condition completely uniform throughout:

$$e_{i,j} = f_{i,j}(\rho_g) \qquad \text{equation 1}$$

where $e_{i,j}$ is the measured electrical capacitance between electrode number i of total N and electrode j of N. $f_{i,j}$ is a simple function such as a polynomial fit between capacitance and density value and $\rho_g$ is the gas density at the pressure in the test pipe. In this simple example, $f_{i,j}$ is equivalent to the forward model functions F and G described earlier.

Step 2. Single-Phase Flowrate Measurement 2.1 If all side-by-side pairs (adjacent electrodes in the direction of flow) measure the same value, then the flow is single-phase, because any flow material (liquid or solid) present will tend to be towards the bottom of the pipe under normal conditions of gravity. In this case the values from ring of electrodes R1, one or more diameters upstream represent the upstream fluid density $\rho_{g1}$ while the values from ring of electrodes R3 represent the fluid density $\rho_{g3}$ at the throat (known as the vena contracta) of the orifice plate. From simple fluid mechanics equations, we know that in a horizontal compressible flow:

$$\text{conservation of mass: } \rho_{g1} \cdot v_{g1} \cdot a_1 = \rho_{g3} \cdot v_{g3} \cdot a_3 \quad \text{equation 2}$$

$$\text{conservation of energy: } \rho_{g1} \cdot (v_{g1})^2 = \rho_{g3} \cdot (v_{g3})^2 \quad \text{equation 3}$$

where $a_1$ and $a_3$ are the area of the flow at positions R1 and R3 and $v_{g1}$ and $v_{g3}$ are the gas velocities at the same positions.

2.2 We calculate $$\rho_g = f^{-1}{}_{i,j}(e_{i,j}) \quad \text{equation 4}$$

at each position R1, R3 (as a minimum, we may also do this at a larger number of electrodes R2, R4, R5 etc. for increased accuracy) where $f^{-1}{}_{i,j}$ is the inverse function of $f_{i,j}$ and is equivalent to the forward model functions F' and G' described earlier.

2.3 Since the areas $a_1$ and $a_3$ are known by design of the pressure device and $\rho_{g1}$ and $\rho_{g3}$ have been calculated from the set of measurements represented by equation 4, we have two equations (2 and 3), 6 unknowns and four knowns, enabling us to calculate the two velocities $v_{g1}$ and $v_{g3}$.

2.4 The mass flowrate of gas is thus given by:

$$m_g = \rho_{g1} v_{g1} \cdot a_1 = \rho_{g3} v_{g3} a_3 \quad \text{equation 5}$$

Equations 1 to 5 are equivalent to the non-linear functions for storage in memory 21 described above in general terms as F, G and Q.

The method in accordance with the invention may be implemented after calibration as follows.

Provide a pressure drop device for example a constrictor/orifice plate 8 etc. at the pipe 2.

Mount a set of any number of electrodes 6, coils or other sensing elements around the flow of interest these elements are arranged such that many pairs of measurements can be made. There may be typically 2 to 5 rings of 8 sensing elements so that N, the number of sensing elements may be on the order of 16 to 40 and there are Nx(N−1) measurements. The sensing elements should be distributed such that some pairs are close together in different areas of the pipe or vessel and that other pairs are separated by at least 1 pipe diameter from, and on either side of the pressure drop device.

The total number of electrodes, coils or other sensing elements is N. There are Nx (N−1) different combinations of measurements between sensing elements. So for 8 sensing elements there are 8×7=56 pairings measuring the electrical properties between elements (1,2), (1,3), (1,4) . . . (2,1), (2,3) . . . (8,7).

Each measurement is affected in a different way by different physical parameters of the flow. For example, the measurement from a pair of elements close together is dominated by the region local to their common boundary, while for element pairs far apart the measurement is determined by conditions across a large part of the volume of the pipe or vessel. The near pair measurement at the bottom of the pipe will be affected more by any liquid or solid loading than a near pair at the top of the pipe or a far-apart pair, while the far-apart pair measurements will be dominated by the fluid density and liquid loading in the far field away from the pressure drop device.

Thus, the parameters of the flow directly influence the measurements in a way that may be extracted by considering the weight that each parameter has on each pairing.

The physical parameters of interest in the flow of dispersed multiphase flow such as wet gas or solids conveying are the flowrates of each phase expressed in kg/s or similar units. Typically, 2, 3 or 4 phases or flow components are present so 2, 3, or 4 outputs are required. Thus, few outputs are required from the many (Nx(N−1)) measurements available from the present invention.

The Nx(N−1) measurements are processed by a processer 9 of FIG. 1 using a set of algorithms that provide a multi-parameter fit to output the few required key output flowrates. This processing may be by means of simple multi-variable regression analysis, an artificial intelligence system, or some other set of mathematical algorithms.

3. Calculation of Flowrate In Wet Gas or Solids 3.1 Compare the electrode measurements from side-by-side pairs in each ring. If there is a second phase present, then there will be a substantial difference between pairs at the top of the pipe and those at the bottom.

3.2 Calculate the probability density function of all side-by-side values in plane R1, and use the measurement value at peak A (stated here as $e_A$) as the equivalent gas value, and peak B as the equivalent second phase value.

$$\rho_g = f^{-1}{}_{i,j}(e_A) \quad \text{equation 6}$$

3.3 Calculate a first guess of the flowrate of gas using the calibration method in step 2.

3.4 Using the single-phase functions $f_{i,j}$, calculate the predicted measurement values $e'_{i,j}$ through the various rings of the sensor which will be different from the values measured directly. This step requires a fluid mechanics model which may be a simple one of a full computational calculation using a commercial computational fluid dynamics software package or other fluid mechanics modelling means. The inputs to the fluid mechanics model include the first guess calculation of density from equation 6 and the first guess estimate of second phase concentration from equation 7.

$$\rho_l = f^{-1}{}_{i,j}(e_B) \quad \text{equation 7}$$

3.4 Considering the two phases to flow independently (the so-called separated flow model) we can calculate gas and liquid flowrates using these new density estimates and equations in step 2.

3.5 The set of $f'_{i,j}$ for a wet gas will be different from the set calculated in single-phase because the electrical field and the fluid mechanics field will be affected by the presence of a second phase. Using a mathematical artificial neural network in a processor these differences are used to calculate a new set of $f'_{i,j}$ to minimise the difference between the set of measured $e_{i,j}$ and the calculated $e'_{i,j}$.

3.7 Repeat step 3.5 until the values of $f'_{i,j}$ converge to an acceptable level and the full flowrate of both phases can be calculated from the simple two-phase model used in 3.4.

4. Calculation of Flowrate in Wet Gas or Solids Conveying

The embodiment in FIGS. 10A and 10B has significant commercial advantages, but the mechanism is equivalent to the above. In this case the side-by-side measurements are related to local conditions, while the 'across-the-pipe' pairs have a much greater depth of penetration along the pipe by a diameter or more.

The side-by-sides can therefore be treated as equivalent to ring R3, while the distant pairs where (i,j) is (1,5), (2,6), (3,7), (4,8) represent the density of the fluid at positions equivalent to R1. Otherwise the process of calculation remains the same as above.

Figure 13:
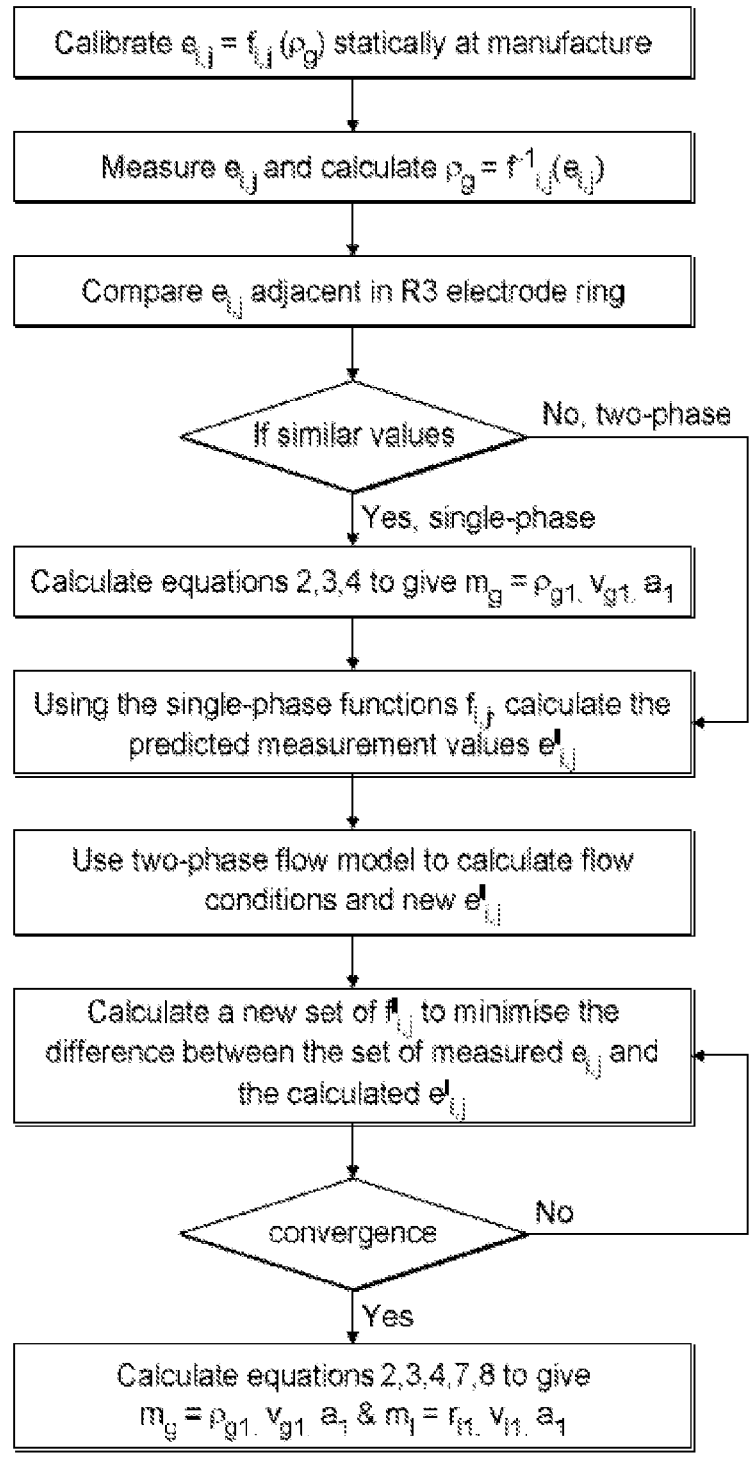
FIG. 13 is an explanatory diagram describing the method in accordance with a preferred embodiment.

FIG. 13 provides a flow chart of the method in accordance with the invention as described above.

In the above described embodiments, there is created a fluid flow within a pipe.

The invention in its broadest aspect may be used to determine a volume of a fluid within a pipe, tank or vessel. That is to say, the fluid is not required to flow but is stationary, or made to flow as the tank moves. A satellite tank may be provided with electrodes, as earlier described, and the described method applied to determine tomographic pixelated images of the permittivity distribution which are processed to determine the density of the fluid present and or other properties. From this, the amount of fluid present in the tank will be determined.

Figure 14A:
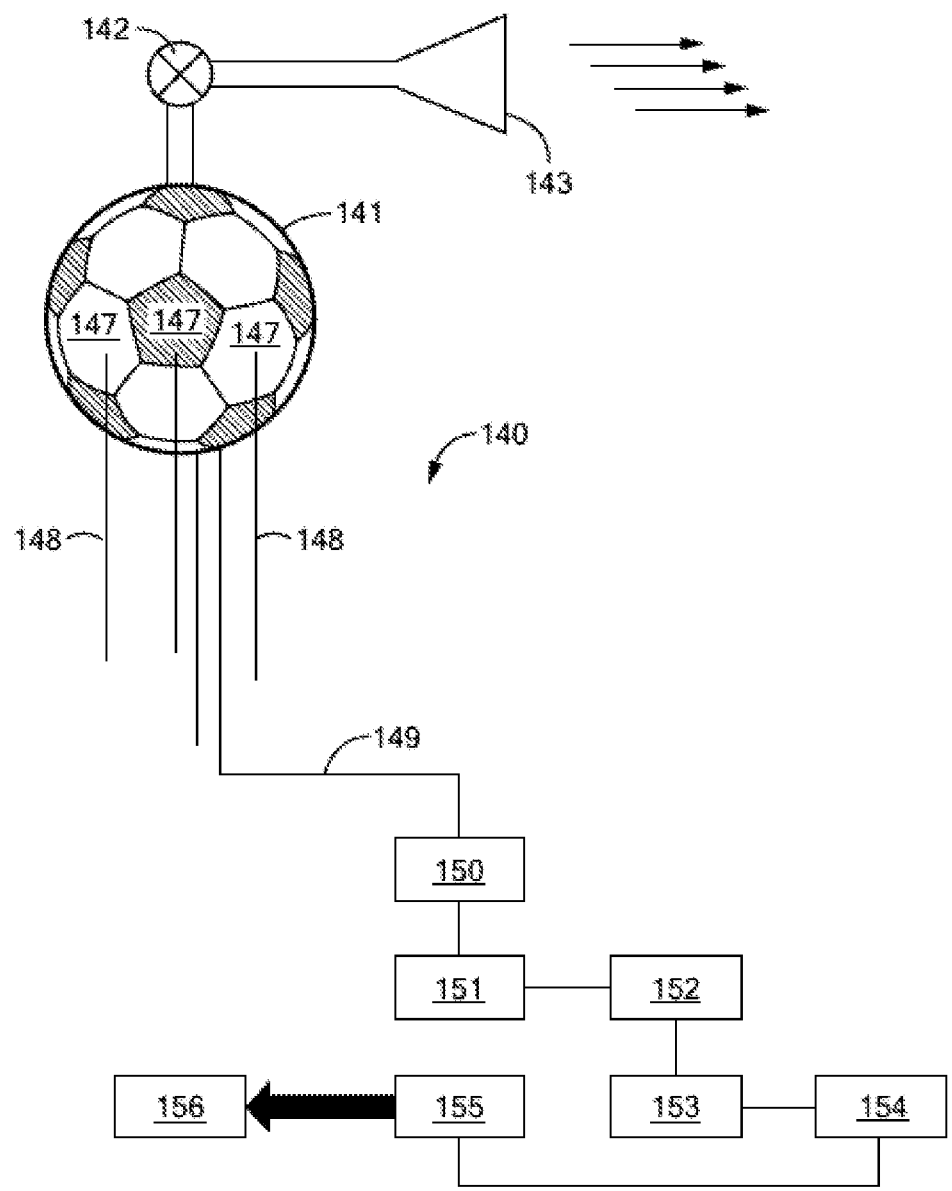
FIGS. 14A and 14B show a further embodiment of the invention for determining the amount of propellant within a storage vessel within a spacecraft.
Figure 14B:
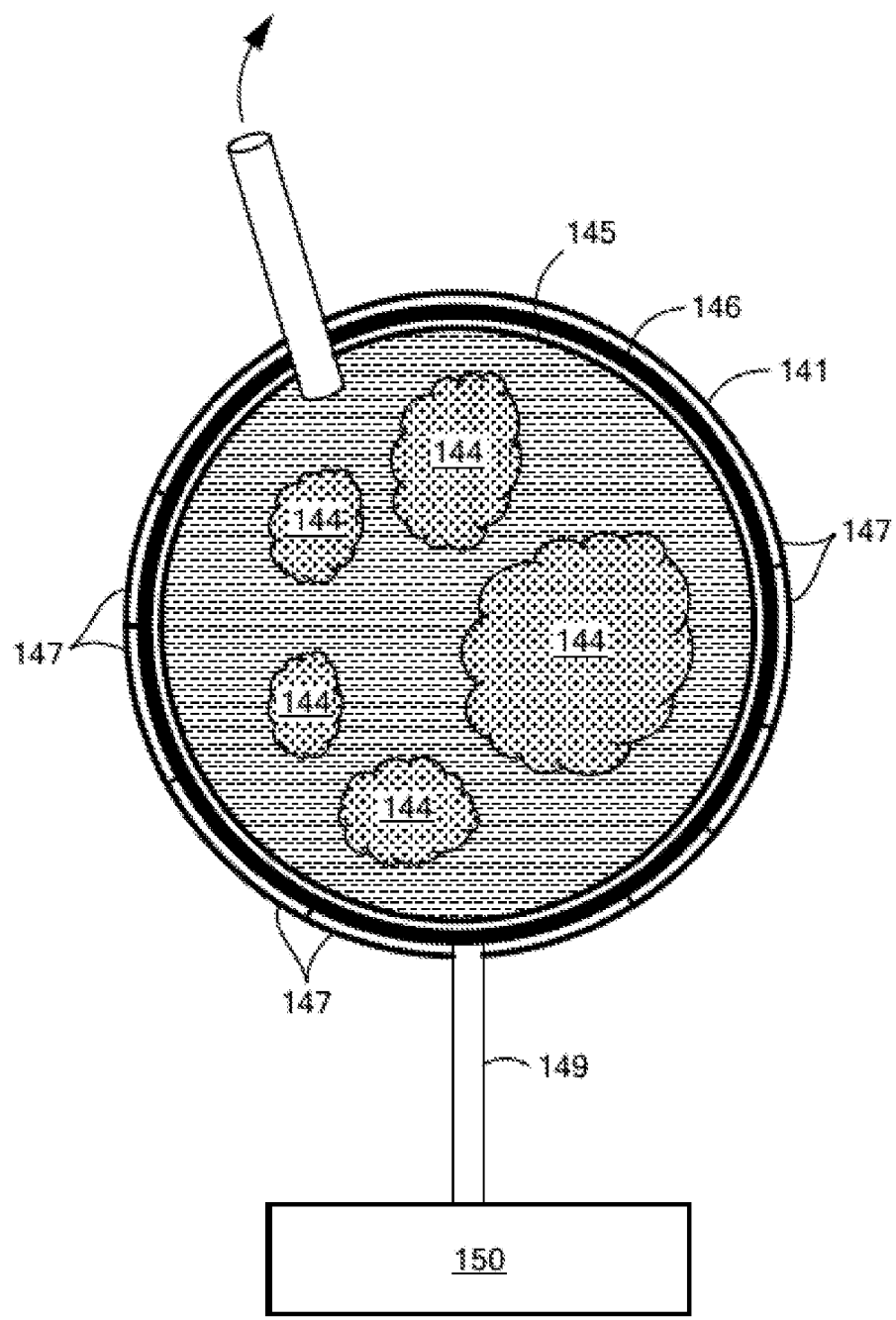

FIG. 14A shows in schematic form a system 140 for determining the amount of fuel remaining in a satellite fuel tank 141. The fuel tank 141 holds a propellant to be delivered via a control valve 142 and hence to a maneuvering nozzle or "thruster" 143 mounted to the exterior surface of the satellite (not shown). This provides a thrust to position the satellite as desired. As is shown in FIG. 14B, the fuel tank 141 contains the fuel 144 within a substantially spherical void. When the satellite is first positioned in orbit the tank 141 is full and as the fuel is used it breaks up into globules or droplets floating under zero gravity conditions within the tank 141. This may be a mixture of different types of fluids making up the fuel or fluid and space between. It will be appreciated that the globules will break, form and reform in a complex matter. They may become stationary due to friction and surface tension or move as a result of movement by the satellite or as a result of flow to the thruster 143.

The tank 141 is formed with an inner electrically insulating layer 145 within a metal wall 146. About the periphery of the tank are fixed a plurality of electrodes 147. These are five sided segments fixed to the tank in an insulating matrix to insulate them one from the other. The segments are better shown in FIG. 14A where they are depicted with dark and light shading to allow them to more easily perceived. The electrodes are formed of electrically conductive, material such as copper or gold. Each electrode is connected by a wire 148 to a bus 149.

The bus 149 connects the electrodes to a capacitance measuring device 150. This is a microprocessor based processing device programmed by software to perform the required capacitance measuring process. This measures the capacitance across various combinations of the electrodes to provide a range of capacitance values across the volume of the tank. These values will be determined in part by the mixture of fuel in droplets and the intervening volumes as shown in FIG. 14B which will enable a picture or image of the make-up of the volume to be determined. This is performed by a tomographic imager 151.

The tomographic imager 151 creates a set of tomographic pixelated images of the permittivity distribution within the mixture from each set of measured capacitances at each point in time. Thus, over time, these "images" are output to memory 152.

Memory 152 is coupled to a density function generator 153 for generating a set of probability density functions for the value of each pixel location within the pixelated images against time. These density functions are then output to memory 154.

A processor 155 for deriving the density or other physical or chemical property of the two fluids from the stored probability density functions is coupled to the memory. The derived density or other parameter is output to another system 156 such as a fuel management system.

The various processes carried out in this embodiment will be apparent from the earlier described embodiments.

In the described embodiments, it will be appreciated that the processing functions may be provided by one, or a number of, microprocessors operating under software control.

It will be appreciated that the person skilled in the art may envision many variations to the above described embodiments without departing for the generality thereof and the scope and spirit of the invention as described in the accompanying claims.

We claim:

1. A method for determining a flow of a fluid comprising the steps of: providing an arrangement of electrodes to, in use, be exposed to a fluid flow; providing a first model of a fluid flow for a particular arrangement of electrodes; providing a set of penalty functions; providing the fluid flow; determining from the electrodes a set of capacitance values; deriving from the set of values and the first model a second model of fluid flow; comparing the second model of fluid flow with the set of values to provide a global system penalty; and comparing the global system penalty with a predetermined threshold value and, responsive to the comparison, modifying the first model or outputting a rate of flow determined from the set of values and the second model of fluid flow.

2. A method as claimed in claim 1 wherein the penalty functions are a difference between a predicted set of capacitances and measured set of capacitances.

3. A method as claimed in claim 2 wherein the first model is a reverse model of flow conditions relative to potential electrode capacitance values.

4. A method as claimed in claim 2 wherein the second model is a forward model of measured electrode capacitance or resistance values relative to flow conditions.

5. Apparatus for determining fluid flow comprising: an arrangement of electrodes to, in use, be exposed to a fluid flow; a first model of a fluid flow for the arrangement of electrodes; a set of penalty functions; a processor responsive to the outputs of the electrodes to determine a set of values representative of electrical properties therebetween capacitance or resistance; a modeller to derive from the set of values and the first model a second model of fluid flow; a comparator to compare the second model of fluid flow with the set of values to provide a global system penalty; and a comparator to compare the global system penalty with a predetermined threshold value and a processor responsive to the comparison for modifying the first model or outputting a rate of flow determined from the set of values and the second model of fluid flow.

6. Apparatus as claimed in claim 5 wherein the penalty functions are a difference between a predicted set of values and the measured set of values.

7. Apparatus as claimed in claim 5 wherein the first model is a reverse model of flow conditions relative to potential set of values provided by the electrodes.

8. Apparatus as claimed in claim 5 wherein the second model is a forward model of measured electrode capacitance values relative to flow conditions.

9. Apparatus as claimed in claim 5 wherein the electrodes are disposed either side of a constriction in the flow.

10. Apparatus as claimed in claim 5 wherein the electrodes are provided, at least in part, on a restriction placed in the flow.

* * * * *